United States Patent [19]

Kloepfer et al.

[11] Patent Number: 4,476,859

[45] Date of Patent: Oct. 16, 1984

[54] FREE ARM SHOULDER SLING

[76] Inventors: Eleanor A. Kloepfer; Katharine A. Fox, both of 7795 W. 120th Ave., Broomfield, Colo. 80020

[21] Appl. No.: 364,057

[22] Filed: Mar. 31, 1982

[51] Int. Cl.³ .......... A61F 5/04

[52] U.S. Cl. .......... 128/87 B; 128/94

[58] Field of Search .......... 128/77, 94, 87 B, 165, 128/DIG. 15, 95; 2/16

[56] References Cited

U.S. PATENT DOCUMENTS

| | | | |
|---|---|---|---|
| 114,615 | 5/1871 | Smitley | 128/94 |
| 1,267,142 | 5/1918 | Stovers et al. | 128/94 |
| 3,515,131 | 6/1970 | Stevens | 128/94 |
| 4,198,964 | 4/1980 | Honneffer | 128/94 X |

OTHER PUBLICATIONS

A. Thorndike, *Athletic Injuries, etc.,* 1942; Orthopedic Support Atlas, p. 335.

*Primary Examiner*—Stephen C. Pellegrino
*Attorney, Agent, or Firm*—Henderson & Sturm

[57] ABSTRACT

This invention relates to sling type supports in general, and more specifically to a sling support specifically designed to immobilize and provide support for a person having a seperated shoulder. In addition, this device is designed to be worn under clothing, and attached to the users body only in the vicinity of the neck and shoulder, and furthermore, can be installed on the users person, using only the unaffected arm.

5 Claims, 8 Drawing Figures

20 23 21 40 43 10 30 31 33

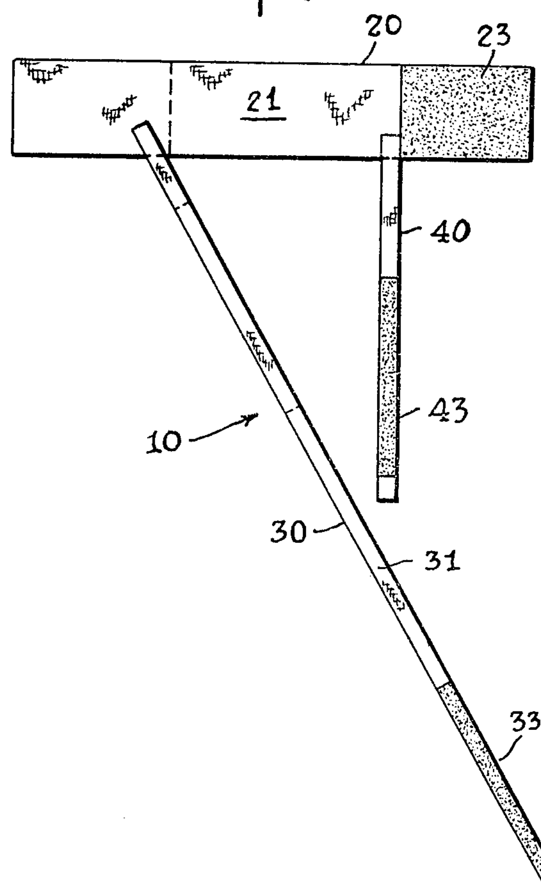
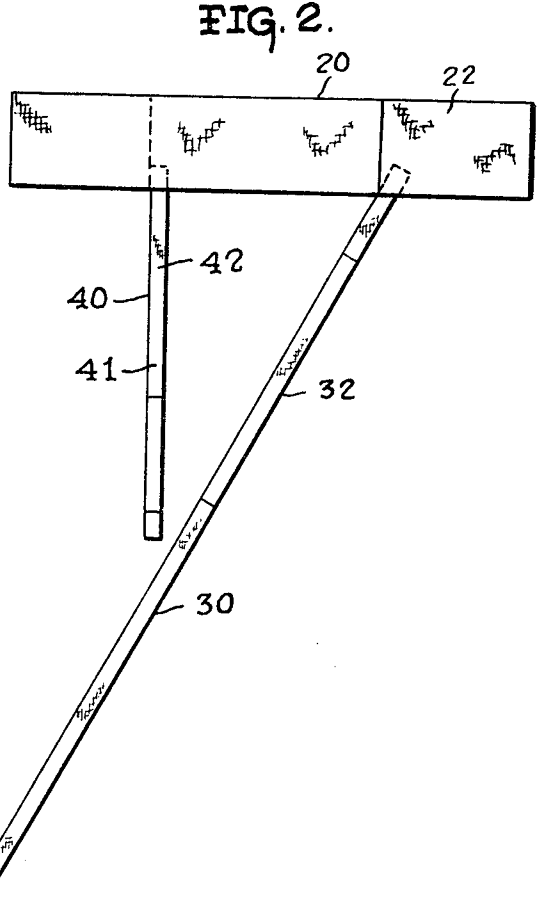
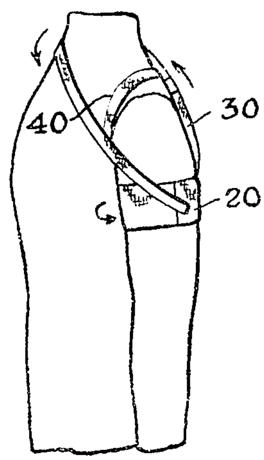
FIG. 3.
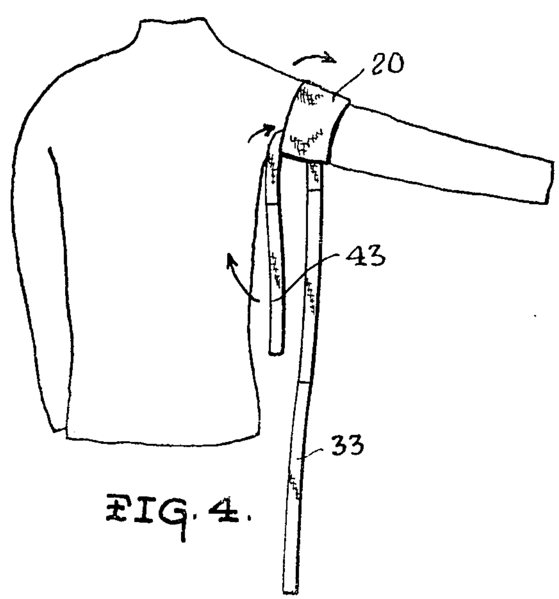
FIG. 4.

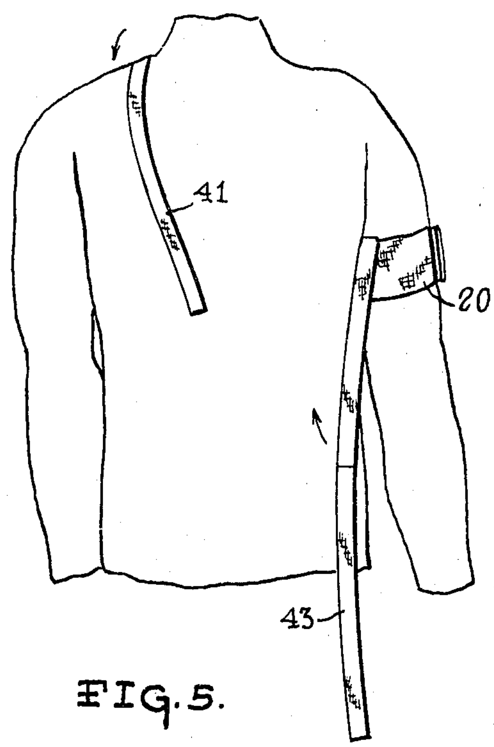
FIG.5.
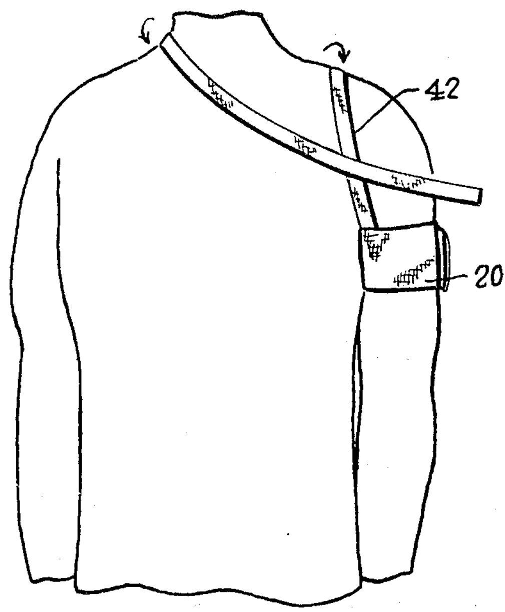
FIG.6.
FIG.7.
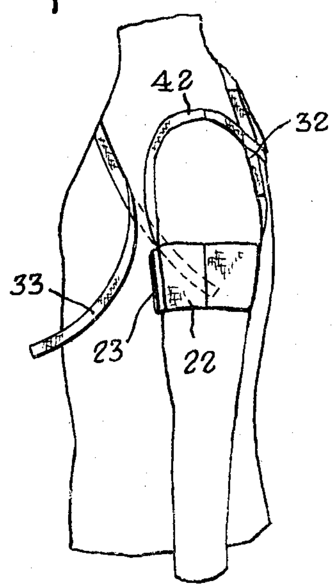
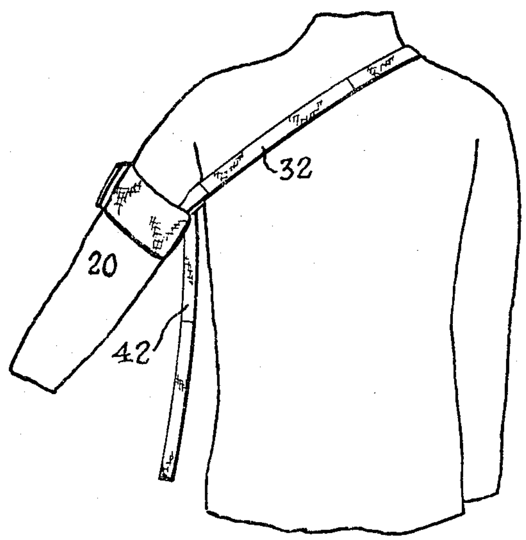
FIG.8.

FREE ARM SHOULDER SLING

BACKGROUND OF THE INVENTION

There are many sling or brace type apparatus present in the prior art, for supporting and immobilizing an arm or shoulder; examples of which can be seen by reference to U.S. Pat. Nos. 4,214,579; 3,404,680; 3,103,216 and 4,188,944.

While the aforementioned, and similar devices, are adequate for their intended purpose, they do share one major inherent dificiency, in that they all must be worn outside of a persons clothing, in order to function in their intended manner. Another common problem with this type of device is that they immobilize the arm to such an extent, that the user cannot exercise the affected limb while the brace or sling is in place. In addition, the prior art devices are usually so complex in their construction, that the user cannot affix the brace to their bodies without assistance from another person.

A common affliction among stroke victims is a subluxed or separated shoulder. While there are some instances where surgery can correct this condition, there are many more instances where surgery is neither practical nor desirable.

As a result, people who suffer from inoperable subluxed shoulders, have in the past, had to be satisfied with the slings or braces which were available, along with their attendant drawbacks.

The present invention however, addresses the problems presented by the prior art devices, and solves them with a simple sling arrangement, that is particularly well suited for this type of an affliction.

BRIEF DESCRIPTION OF THE DRAWINGS

FIG. 1, is a front plan view of the interior surface of the free arm sling.

FIG. 2, is a front plan view of the exterior surface of the free arm sling.

FIG. 3, is a perspective view of the free arm shoulder sling in its fully assembled relationship.

FIGS. 4 thru 8, illustrate the free arm shoulder sling in various stages of assembly.

SUMMARY OF THE INVENTION

An object of the present invention is the provision of a brace or sling specifically designed to alleviate the pain and discomfort associated with a sub-luxed or separated shoulder.

Another object of the present invention is the provision of a shoulder sling, which can be worn under any type of outer garment, so that it will not be apparent to the casual observer that the user is suffering from any kind of infirmity.

Still another object of the present invention is the provision of a simple shoulder sling which the user can attach using only one arm.

A further object of the present invention is the provision of an inexpensive, easily fabricated shoulder sling, which will avoid the problems associated with prior art devices.

A still further object of the present invention is the provision of a shoulder sling, which provides support and immobilization of the users shoulder immediately adjacent to that portion of the users anatomy.

Yet another object of the present invention is the provision of a shoulder sling or brace which not only provides relief, comfort and support for the users shoulder, but also leaves the remaining portion of the users arm free to perform theraputic exercises.

Still yet another object of the present invention is he provision of a shoulder sling, which will keep the shoulder separation stabilized when in use, yet is so compact and lightweight that the user will hardly be aware of its presence.

These and other objects, advantages and novel features of the invention will become apparent from the detailed disclosure which follows when considered in conjunction with the accompanying drawings.

DETAILED DESCRIPTION OF THE PREFERRED EMBODIMENT

As can be seen by reference to FIG. 1, the free arm shoulder sling, is designated generally as 10, and comprises three major components. These components consist of a cuff member 20, an elongated neck loop member 30, and a shoulder loop member 40.

The various components as shown in FIGS. 1 and 2, are provided on their interior and exterior surface with VELCRO type cooperating releasable fastening means, whose purpose, function, and specific cooperation, will be explained in detail further on in the specification.

Taking the major components one at a time; the cuff member 20 comprises a wide, elongated, rectangular strip 21 of elasticized material; the neck loop member 30 comprises an elongated thin strip 31 of woven material, and the shoulder loop member 40 comprises a short thin strip 41 of woven material.

As shown in the drawings, the neck loop member is secured to the cuff member at a point approximately one third the distance to one end of the cuff member, and the shoulder loop member is secured to the cuff member at a point approximately one third the distance to the other end of the cuff member. In addition, the neck loop member is attached to and projects from the cuff member at an angle of approximately 45°, while the shoulder loop member is attached to and projects from the cuff member at an angle of 90°.

For the sake of clarity, the cooperating VELCRO type fastening means will be characterixed as "soft" and "hard". The soft fastening means refers to the raised nap surface that is engaged by the plastic bifurcated loops, which comprise the hard fastening means.

With the foregoing in mind, it can be seen that both the neck loop member, and the shoulder loop member, are provided with hard cooperating fastening means on their interior surface adjacent their free ends. In addition, the cuff member is provided with hard cooperating fastening means on its interior surface, adjacent to the end of the cuff member, from which the shoulder loop member projects.

As shown in FIG. 2, the exterior surface of the cuff member is provided with soft fastening means on its exterior surface adjacent the end of the cuff member, from which the neck loop member projects. In addition, both the neck loop member and the shoulder loop member are provided with soft cooperating fastening means on their exterior surface adjacent the cuff member.

The shoulder loop member 40 in the preferred embodiment is provided with both hard 43 and soft 42 fastening means on opposite sides, which are secured to the strip of material 41, by any suitable means such as stitching, adhesives, etc. The exterior surface of the shoulder loop is provided with a soft fastening means 42, which extends from a point adjacent to the cuff member to a point past the mid-point of the shoulder strip 41. The interior surface of the shoulder loop member is provided with a hard fastening means 43, which extends from a point adjacent to the free end of the shoulder loop member, to a point past the mid-point of the shoulder loop member; so that both the hard 43 and soft 42 fastening means are disposed on opposite sides of the shoulder loop member, in an overlapping relationship.

The neck loop member 30 in the preferred embodiment, likewise is provided with hard 33 and soft 32 fastening means on opposite sides, which are secured to the strip of material 31 in any suitable manner. The exterior surfact of the neck loop is provided with a soft fastening means 32, which extends from a point adjacent the cuff member 20, to a point at least one-third the distance from the cuff member to the free end of the neck strip 31. The interior surface of the neck loop 30 is provided with a hard fastening means 33, which extends from a point adjacent the free end of the neck loop, to a point at least one-third the distance from the free end of the neck loop to the cuff member.

At this point it should be noted that while both the neck and shoulder loop members may be provided with hard and soft fastening members, on their respective sides, which run the entire length of both the neck strip 31 and the shoulder strip 41, this is neither necessary nor desirable for the operation of the sling, and will only add to the cost of manufacture thereof, without improving the function or operation.

The cuff member 20 in the preferred embodiment is also provided with hard 23 and soft 22 fastening means, which are secured to the cuff member by any suitable means. The soft fastening means 22 are disposed on the exterior surface of the cuff member and extend from a point adjacent to the elongated neck strip 31, to the end of the cuff member proximate thereto. The hard fastening means 23 are disposed on the interior surface of the cuff member and extend from a point adjacent to the short shoulder strip 41, to the end of the cuff member proximate thereto.

While the exact dimensions of the sling components will change to accommodate different sized individuals, the relative proportions of the components will remain the same. The cuff member 20 in the preferred embodiment is approximately the same length as the shoulder strip and approximately three times the width of the neck strip or the shoulder strip. In addition, the elongated neck strip is approximately twice the length of either the cuff member or the shoulder member.

The disposition of the free arm sling 10 on a users person is illustrated in FIGS. 3 thru 8. FIG. 4, shows the cuff or arm encircling member 20 in its fastened relationship, on the users arm, in the vicinity of the arm pit. In order for the sling to function properly, the cuff member 20 of the sling must be placed as high up on the arm as in comfortable for the user. Since the cuff member is formed from elasticized material, the cuff member can be secured as simply as the user desires, using the hard 23 and soft 22 releasable fastening means on the interior and exterior surfaces of the cuff member respectively, in a well recognized manner. As shown in FIG. 4, at this stage of the assembly of the sling, the neck loop will be positioned at the rear of the cuff member and the shoulder loop will be positioned at the front of the cuff member, and both the neck and shoulder loops will be supported by the top of the cuff member.

The next step in the assembly of the device is to bring the neck loop 30 around the back of the user, and around the neck of the user, on the side of the neck opposite from the affected shoulder. FIG. 5, shows how the sling would appear at this point viewing the user from the front, and FIG. 8 illustrates how the sling would appear from the rear.

Refering now to FIG. 6, it can be seen that the next step in the assembly of the sling is to bring the shoulder loop up over the affected shoulder, so that the soft fastening means 42 faces away from the users chest, and the hard fastening means 43 cooperates with the soft fastening means 32 on the shoulder strip, to secure the shoulder loop to the neck loop.

The final step in the assembly of the sling, requires that the neck loop be brought across the users chest, so that the hard fastening means 30 on the interior of the neck loop, will contact not only the soft fastening means 42 on the exterior of the shoulder loop, but also that portion of the soft fastening means 22 on the cuff member which were not covered when the cuff was assembled.

It should be appreciated by this time, that a sling manufactured in accordance with these teachings will provide three points of support for the affected arm, with two of the support points being supplied by both ends of the neck loop, and the third support point being provided by the secured end of the shoulder loop, via its two containing surfaces with the neck loop.

It should also be apparent, that since the cuff member is positioned adjacent the users bicept/tricept area and the neck and shoulder loop members are secured to the top of the cuff member, that this sling structure will not only support and immobilize the users shoulder, but can be worn under clothing without being noticeable to a casual observer. In addition, the sling can easily be assembled by the user without assistance, and will further allow the arm to undertake physical therapy while the sling is in place.

Having thereby described the subject matter of this invention, it should be obvious that any substitutions, modifications and variations of the device are possible in light of the above teachings. It is therefore to be understood that the invention as taught and described is only to be limited by the breadth and scope of the appended claims.

What we claim:

1. A free arm shoulder sling consisting of:

a generally rectangular arm encircling cuff member comprising a wide strip of elasticized material having a first and second cooperating fastening means, disposed adjacent to ends of the cuff member, and on opposite sides.

a neck loop member disposed adjacent the first of the said cooperating fastening means, and secured on one end to the top of the cuff member, and a shoulder loop member secured on one end to the top of the cuff member and disposed adjacent to the second of the cooperating fastening means; wherein, the neck loop member and the shoulder loop member comprise strips of material which are also provided with a first and second cooperating fastening means disposed adjacent their respective ends and on opposite sides, and the neck loop member comprises an elongated strip of material whose length is approximately twice the length of the shoulder loop member, and the shoulder loop member projects from the cuff member at an angle of 90°, while the neck loop member projects from the cuff member at an angle of other than 90°.

2. A free arm shoulder sling as in claim 1; wherein, all of the said first cooperating fastening means are disposed on the exterior surface of the said members.

3. A free arm shoulder sling as in claim 2; wherein, all of the said second cooperating fastening means are disposed on the interior surface of the said members.

4. A free arm shoulder sling as in claim 3; wherein, the second said cooperating fastening means are further disposed adjacent the free ends of the neck loop member and the shoulder loop member.

5. A free arm shoulder sling as in claim 4; wherein, the first said cooperating fastening means are disposed on the neck loop member and the shoulder loop member adjacent the cuff member.

* * * * *